(12) United States Patent
Turco

(10) Patent No.: US 8,673,585 B2
(45) Date of Patent: Mar. 18, 2014

(54) BIOCHEMICAL SERUM MARKER

(75) Inventor: Maria Caterina Turco, Avellino (IT)

(73) Assignee: Biouniversa S.r.l., Fisciano (SA) (IT)

( * ) Notice: Subject to any disclaimer, the term of this patent is extended or adjusted under 35 U.S.C. 154(b) by 0 days.

(21) Appl. No.: 13/513,766

(22) PCT Filed: Dec. 3, 2010

(86) PCT No.: PCT/EP2010/068836

§ 371 (c)(1),
(2), (4) Date: Jun. 4, 2012

(87) PCT Pub. No.: WO2011/067377

PCT Pub. Date: Jun. 9, 2011

(65) Prior Publication Data

US 2012/0244561 A1 Sep. 27, 2012

(30) Foreign Application Priority Data

Dec. 4, 2009 (IT) .................................. MI09A2154

(51) Int. Cl.
*G01N 33/53* (2006.01)
(52) U.S. Cl.
USPC ........................................ 435/7.94; 435/7.92
(58) Field of Classification Search
None
See application file for complete search history.

(56) References Cited

U.S. PATENT DOCUMENTS

| 7,537,760 B2 | 5/2009 | Leone et al. | ............... 424/130.1 |
| 2005/0176660 A1* | 8/2005 | Leone et al. | ..................... 514/44 |

FOREIGN PATENT DOCUMENTS

| EP | 1323733 | 7/2003 |
| IT | MI2009A002154 | 12/2009 |
| WO | WO 03/055908 | 7/2003 |
| WO | PCT/EP2010/068836 | 12/2010 |

OTHER PUBLICATIONS

Takayama et al., J. Biol.Chem 1999; vol. 274,No.2, pp. 781-786.*
Arimura et al., Num Mutat 2011;32:1481-1491.*
Selcen et al., Annals of Neurology Jan. 2009;vol. 65, No. 1, pp. 83-89.*
Ammirante, M., et al. "IKK{gammal} Protein is a Target of BAG3 Regulatory Activity in Human Tumor Growth." Proc. Natl. Acad. Sci. U.S.A., pp. 1-6 (2010).
Bonelli, et al. "BAG3 Protein Regulates Stress-Induced Apoptosis in Normal and Neoplastic Leukocytes." Leukemia 18, pp. 358-360 (2004).
Bruno, A.P., et al. "Identification of a Synaptosome-Associatecl Form of BAG3 protein." Cell Cycle 7(19), pp. 3104-3105 (2008).
Carra, S., et al. "HspB8 and Bag3: A New Chaperone Complex Targeting Misfolded Proteins to Macroautophagy." Autophagy 4(2), pp. 237-239 (2008a).
Carra, S., et al. "HspB8 Chaperone Activity Toward Poly(Q)-Containing Proteins Depends on its Association with Bag3, a Stimulator of Macroautophagy." J. Biol. Ch;em. 18, 283(3), pp. 1437-1444 (2008b).
Chen, L., et al. "Light Damage Induced Changes in Mouse Retinal Gene Expression." Exp. Eye Res. 79(2), pp. 239-247 (2004).
Chiappetta, G., et al. "The Antiapoptotic Protein BAG3 is Expressed in Thyroid Carcinomas and Modulates Apoptosis Mediated by Tumor Necrosis Factor-Related Apoptosis-Inducing Ligand." J. Clin. Endocrinol. Metab. 92(3), pp. 1159-1163 (2007).
Franceschelli, S., et al. "Bag3 Gene Expression is Regulated by Heat Shock Factor 1." J. Cell Phisiol. 19, 215(3), pp. 575-577 (2008).
Gentilella, A., et al. "Activation of BAG3 by Egr-1 in response to FGF-2 in neuroblastoma cells." Oncogene 28, 27(37), pp. 5011-5018 (2008).
Homma, S., et al. "BAG3 Deficiency Results in Fulminant Myopathy and Early Lethality." Am. J. Pathol. 169(3), pp. 761-773 (2006).
Iwasaki, M., et al. "BAG3 Regulated Motility and Adhesion of Epithelial Cancer Cells." Cancer Res1, 67(21), pp. 10252-10259 (2007).
Kassis, J.N, et al. "CAIR-1/BAG-3 Modulates Cell Adhesion and Migration by Downregulating Activity of Focal Adhesion Proteins." Exp. Cell Res. 10, 312(15), pp. 2962-2971 (2006).
Liao, Q., et al. "The Anti-Apoptotic Protein BAG-3 is Overexpressed in Pancreatic Cancer and Induced by Heat Stress in Pancreatic Cancer Lines." FEBS Lett 503, pp. 151-157 (2001).
Pagliuca, M.G., et al. "Regulation by Heavy Metals and Temperature of the Human BAG-3 Gene, a Modulator of Hsp70 Activity." FEBS Lett 541, pp. 11-15 (2003).
Romano, M.F., et al. "BAG3 Protein Controls B-Chronic Lymphocytic Leukemia Cell Apoptosis." Cell Death Differ. 10, pp. 383-385 (2003a).
Romano, M.F., et al. "BAG3 Protein Regulates Cell Survival in Childhood Acute Lymphoblastic Leukemia Cells." Cancer Biol. Ther. 3, pp. 508-510 (2003b).
Rosati, A., et al. "Apoptosis Inhibition in Cancer Cells: A Novel Molecular Pathway that Involves BAG3 Protein." IJBCB 39, 7-8, pp. 1337-1342 (2007b).
Rosati, A., et al. "Evidence for BAG3 Modulation of HIV-1 Gene Transcription." J. Cell Physiol. 210(3), pp. 676-683 (2007a).
Tabuchi, S., et al. "Surgical Treatment of Arteriocvenous Malformation in a Patient with Human Immunodeficiency Virus Infection and Hemophilia A: Case Report." J. Stroke Cerebrovasc. Dis. 15(2), pp. 66-68 (2006).
International Search Report and Written Opinion issued Apr. 26, 2011 for International Application No. PCT/EP2010/068836, which was filed Dec. 3, 2010 (Inventor—Maria Caterina Turco; Applicant—Biouniversa S.R.L.) (pp. 1-8).

* cited by examiner

*Primary Examiner* — Shafiqul Haq
*Assistant Examiner* — Carmencita M Belei
(74) *Attorney, Agent, or Firm* — Ballard Spahr LLP

(57) ABSTRACT

The present invention relates to a method for detecting the presence and/or concentration of the soluble BAG3 protein in an unknown biological sample and the assay is preferably carried by ELISA assay with antibodies, preferably monoclonal antibodies. The presence of said protein in a soluble form is associated with heart disease or with the presence of pancreatic tumors.

11 Claims, 10 Drawing Sheets a)

100 kDa b)

| Start - End | Observed | Mr(expt) | Mr(calc) | ppm | Miss Sequence |
|---|---|---|---|---|---|
| 32 - 47 | 1915.8500 | 1914.8427 | 1914.9013 | -31 | K.IDPQTGWPFFVDHNSR.T |
| 48 - 55 | 990.3800 | 989.3727 | 989.4567 | -85 | R.TTTWNDPR.V |
| 63 - 73 | 1062.4700 | 1061.4627 | 1061.4738 | -10 | K.DTASSANGPSR.N |
| 78 - 82 | 611.4200 | 610.4127 | 610.4166 | -6 | R.LLPIR.E |
| 109 - 123 | 1764.8800 | 1763.8727 | 1763.8856 | -7 | R.QPHLFHAYSQPGVQR.F |
| 200 - 209 | 1081.5600 | 1080.5527 | 1080.5676 | -14 | R.SSLGSHQLPR.G |
| 256 - 267 | 1481.7300 | 1480.7227 | 1480.7423 | -13 | K.IQGDDWEPRPLR.A |

BIOCHEMICAL SERUM MARKER

CROSS REFERENCE TO RELATED APPLICATIONS

The present application is a National Phase Application of International Application No. PCT/EP2010/068836, filed Dec. 3, 2010, which claims the benefit of Italian Patent Applications No. MI2009A002154, filed Dec. 4, 2009, which applications are incorporated herein fully by this reference.

REFERENCE TO SEQUENCE LISTING

The Sequence Listing submitted Aug. 28, 2013 as a text file named "37428_0001U1_Filed_Sequence_Listing.txt," created on Aug. 22, 2013, and having a size of 2,720 bytes is hereby incorporated by reference pursuant to 37 C.F.R. §1.52 (e)(5).

FIELD OF THE INVENTION

The present invention pertains to the technical field of diagnostic serum markers.

STATE OF THE ART

BAG3 (RefSeq: NP_004272; Gene ID 9531) is a 74 kDa cytoplasmic protein particularly concentrated in the rough endoplasmic reticulum. Recently a 40 kD cytoplasmic form has been described that is associated with synaptosomes (Brown et al., 2008). Moreover, a recombinant form and some deletion mutants were expressed in *E. coli* (Rose et al 2007 (a)).

In human, bag3 gene expression is constitutive in myocytes, in few other normal cell types as well as in some cancers (leukemias and lymphomas, myeloma, pancreatic and thyroid cancer, melanoma, osteosarcoma, etc.) (Romano et al, 2003; Homma et al. 2006; Chiappetta et al., 2007, Rosati et al., 2007) and is induced in various cell types in response to different stressors: pancreatic cancer lines exposed to high temperatures (Liao et al. 2001), HeLa cells incubated with heavy metals or subjected to high temperatures (Pagliuca et al., 2003), leukocytes treated with dietilmaleate, an oxidative stress inducing agent (Bonelli et al., 2004), murine retinal cells damaged by light (Chen et al., 2004), Molt-4 cells (human leukemic T cells) treated with low-intensity ultrasound (Tabuchi et al., 2006), human microglial cells exposed to HIV-1 virus (Rosati et al., 2007 a). These findings indicate that the regulation of BAG3 expression is an important component in the cellular response to stress and is consistent with the presence of elements responsive to the transcription factor HSF (heat shock factor) 1, activated in various forms of cellular stress, in the promoter of the bag3 gene. Modulation of HSF1 activity leads to a significant reduction of the cellular levels of BAG3 protein, indicating that this regulator plays an important role in the expression of bag3 (Franceschelli et al., 2008). EGR1 is another transcription factor involved in regulation of bag3 expression (Gentilella et al., 2008). The first evidence that BAG3 affects survival of primary cancer cells came from studies on primary leukemic cells from 24 patients with B-cell chronic lymphoid leukemia (B-CLL) and 11 children with acute lymphoblastic leukemia (ALL): decreasing BAG3 levels by use of specific antisense oligodeoxynucleotides resulted in more than 100% increase of apoptotic bodies ($p<0.001$) as also described in EP 1465927 A1 and U.S. Pat. No. 7,537,760 B2. Thus the percentage of apoptosis in these cells was significantly increased as compared to both untreated cells and to cells treated with the same chemotherapy drugs (Leone and Turco, 2001, Romano et al., 2003a, 2003b). In normal leukocytes, overexpression of the gene proved to reduce significantly the apoptotic response (Bonelli et al., 2004). Subsequently, an analysis of human thyroid tissue showed that normal tissue and goiter samples tested negative for BAG3 expression, while cancer samples tested clearly positive, and a higher BAG3 expression was observed in anaplastic tumors.

In other tumors, such as osteosarcoma and melanoma cells, bag3 specific siRNAs cause reduced survival of basal cells, showing a remarkable synergistic effect with chemotherapeutic agents; BAG3 knockdown in human melanoma cells implanted in mice reduced significantly tumor growth, with improved survival of animals (Ammirante et al., in press). On the other hand, bag3 overexpression results in decreased apoptosis of cancer cells treated with chemotherapy drugs or exposed to other pro-apoptotic stimuli (Rose et al., 2007 (b)).

Although the presence of cytoplasmic BAG-3 has been detected in different cell systems and was found associated with tumors, e.g. leukemia or thyroid cancers, as well as more generally to cell survival, to date a soluble form of BAG3 was never described, and its presence in the serum was never associated with states of cardiac distress.

Therefore, the present invention solves the problem of the identification of a new secreted soluble form of the BAG-3 protein and of its production in humans and other mammals, which is associated with specific disease states in a surprisingly specific and sensitive manner.

SUMMARY OF THE INVENTION

The present invention relates to a method for detecting the presence and/or concentration of soluble BAG3 protein in an unknown biological sample, comprising the following steps:
a. obtaining a biological sample, consisting of serum or plasma,
b. determining the presence or concentration of soluble BAG3 in the biological sample,
c. comparing the values obtained from a sample with reference values or with values obtained from biological reference samples,
d. optionally, determining further groups of similar values (and possibly their further division into groups with statistically different mean values),
e. associating the presence and/or the level of soluble BAG3 to a pathological condition, where the condition is a heart disease or pancreatic cancer.

Preferably the dosage step (b) is performed by ELISA with antibodies, preferably monoclonal. Alternatively, the soluble protein can be isolated from the serum of patients.

The proposed assay method allows a statistically significant separation of the group of cardiac patients from the group of healthy people, preferably in groups of comparable age. It can also stratify such patients with heart disease in subgroups of patients at increased risk (heart failure, HF).

DETAILED DESCRIPTION OF THE INVENTION

Figure 1:
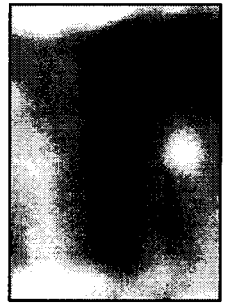
FIG. 1. Immunohistochemical section showing expression of the BAG3 protein in normal heart tissue and after induction of infarction in rats.

The present invention is based on the finding of a soluble form of the BAG3 protein with an unexpected biological activity compared to the function previously described for the intracellular form (regulation of cell cycle and apoptosis): for example such form, actively secreted by cells, can activate monocytes/macrophages.

It was found that the soluble form is also a serum biochemical marker that is highly specific for certain pathological conditions, especially heart disease and pancreatic cancer. Therefore the object of the present invention is the soluble form of the BAG3 protein and methods to verify its levels in a biological sample consisting of serum, in order to determine the presence of the above mentioned pathological situations.

For soluble BAG3 it is meant a form of BAG3 that is actively secreted by cells, as shown, for example, by its association with exosomes in pancreatic cancer cells (Panc-1) and by its presence in the supernatant of viable tumor cell lines (by Trypan Blue exclusion assay) such as Hep G2 cells (human hepatocellular carcinoma), C6 cells (rat glioblastoma), ASPC-1 cells (human pancreatic adenocarcinoma), ARO cells (anaplastic thyroid carcinoma), HT-29 cells (colorectal adenocarcinoma) and the very same Panc-1 cells, thus showing that soluble BAG3 does not originate by release of cellular contents in the culture medium upon cell death.

Moreover, soluble BAG3 is released (or secreted) following induction of oxidative stress in cardiomyocytes and can be quantitatively purified as a form with a molecular weight around 75 kD, for example by SDS-PAGE, from the serum of patients with heart disease.

Therefore, in a biological sample, soluble BAG3 can be distinguished from the cytoplasmic form because its presence is independent from the presence of cells.

In fact, for example, the BAG3 protein is found to be higher in thyroid tumor biopsies than in the normal tissue, but immunohistological staining detects the protein only in the cytoplasm.

In accordance with the use of soluble BAG3 as serum marker for a pathological condition, the invention relates to a method for detection of the presence and of the amount of such form by use of monoclonal or polyclonal antibodies as preferred capture and/or detection agents.

Monoclonal and polyclonal anti-BAG3 antibodies are described in EP 1465927 A1 and U.S. Pat. No. 7,537,760 B2.

According to a preferred realization the method comprises the following steps:
a. obtaining a biological sample, consisting of serum or plasma,
b. determining the concentration of soluble BAG3 in such biological sample
c. comparing the results obtained from the sample with reference values or with values obtained from reference serum samples,
d. optionally, determining subgroups of patients with soluble serum BAG-3 mean values that are not statistically different (for example, a group of patients 21-43 years of age and a group 44-65 years of age),
e. associating the levels or the presence of soluble BAG3 with a pathological condition selected among heart disease or pancreatic cancer.

The definition heart disease refers to angina pectoris, unstable angina, myocardial infarction, heart failure, acute coronary disease, acute heart failure, chronic heart failure, and iatrogenic heart disease.

According to a preferred realization the biological sample is serum or plasma and is of human origin. It can also be obtained from whole blood, optionally supplemented with substances, e.g. with anti-coagulant activity.

The presence of BAG3 in the biological sample is preferably determined by immunological methods and even more preferably with anti-BAG3 monoclonal, polyclonal or recombinant antibodies (e.g. ScFv fragments, diabodies, etc.). According to a preferred realization the antibodies are monoclonal and recognize epitopes in the BAG3 sequence (RefSeq: NP_004272; Gene ID 9531) including fragment 18-33, 385-399 or 533-547. The antibodies are even more preferably those identified in U.S. Pat. No. 7,537,760 or subclones of the parental hybridoma No. PD02009, deposited on Dec. 17, 2002 at the Advanced Biotechnology Center of Genoa, described herein; alternatively, they may be derivatives of such antibodies, such as recombinant and/or humanized forms.

According to a further realization, commercial anti-BAG3 antibodies can also be used (e.g.: Goat Anti-Bag3 Polyclonal Antibody, Abcam; Rabbit Anti-Bag3 Polyclonal Antibody, Abcam; Mouse Anti-Bag3 Monoclonal Antibody, Abcam; Rabbit Anti-Human Bag3 Polyclonal Antibody, Abcam; Mouse Anti-Human Bag3 Monoclonal Antibody, Clone 5A8, Abgent; Anti-Bag3 Polyclonal Antibody, Abnova Corporation; Goat Anti-Bag3 Polyclonal Antibody, Abnova Corporation; Mouse Anti-Bag3 Polyclonal Antibody, Abnova Corporation; Rabbit Anti-Human Bag3 Polyclonal Antibody, Atlas Antibodies; Goat Anti-Bag3/BIS/CAIR1 Polyclonal Antibody, Everest Biotech; Goat Anti-Bag3 Polyclonal Antibody, GeneTex; Rabbit Anti-Human Bag3 Polyclonal Antibody, GeneTex; Goat Anti-Human Bcl-2-bindin Protein BIS (BAG3) Polyclonal Antibody, LifeSpan BioSciences; Rabbit Anti-Human Bcl-2-bindin Protein BIS (BAG3) Polyclonal Antibody, LifeSpan BioSciences; Goat Anti-Bag3 Polyclonal Antibody, Novus Biologicals; Mouse Anti-Human Bag3 Polyclonal Antibody, Novus Biologicals; Rabbit Anti-Bag3 Polyclonal Antibody, Novus Biologicals; Rabbit Anti-Human Bag3 Polyclonal Antibody, Novus Biologicals; Goat Anti-Human BAG3/BIS/CAIR1 Polyclonal Antibody, Raybiotech, Inc.; Rabbit Anti-Human Bag3 Polyclonal Antibody, Proteintech Group, Inc.; Rabbit Anti-Human BAG3 Prestige Antibodies Powered by Atlas Antibodies Antibody, Sigma-Aldrich; etc.), preferably if they are monoclonal.

The immunological assay is preferably ELISA, where the first capture ligand is an antibody, even more preferably selected from monoclonal antibodies that recognize epitopes in the sequence of BAG3 corresponding to aa 18-33, 385-399 or 533-547; the second antibody for detection, that recognizes an epitope different from that recognized by the capture antibody, may be a monoclonal, a mixture of at least two monoclonal antibodies or a polyclonal antibody.

Although the preferred realization of the assay involves the use of anti-BAG3 antibodies, the same result can be achieved with BAG3 binding molecules other than antibodies, for example soluble receptors or natural or synthetic ligands.

The ligand used for detection can in turn be recognized by antibodies, e.g. antibodies labelled with fluorophores, chromophores or enzymes capable of converting a substrate into a chromophore, hence useful to visualize the presence of BAG3 in the biological sample; alternatively it can be directly linked to such chromophore groups.

Different reaction schemes can be identified that are equally valid to detect and/or measure the level of soluble BAG3. For example it is possible to use, for capture, a first antibody, e.g. an anti-BAG3 monoclonal, preferably selected from monoclonal antibodies produced by the parental clone PD2009 (AC-1, AC-2 or AC-3 which recognize a single epitope of the BAG3 sequence, and in particular the amino acid sequence from amino acids 18-33, 385-399 or 533-547, respectively). For detection, it is possible to use a second antibody which can be a monoclonal or a polyclonal antibody (if it is polyclonal, the antibody is preferably named TOS-2, as described by Rosati et al., 2007 (a), raised against the entire recombinant protein used as immunogen) or a monoclonal antibody obtained from the parental clone PD2009 but different from the antibody used for capture, such as, for instance, AC-2 or AC-3, or a mixture of the two, which recognize epitopes that are different from the epitope recognized by AC-1 (corresponding to the amino acid sequences 385-399 and 533-547 of the BAG3 protein, respectively). A person skilled in the art can determine the variations of the above BAG3 capture and/or detection schemes which are however included in the present invention even if monoclonal or polyclonal antibodies are used that are different from those described for the preferred realizations of the assay. For example, the method comprises the use of antibodies derived from the above described monoclonal antibodies, such as those expressed in recombinant form (such as, for example, ScFv fragments, minibodies, diabodies etc.) or modified, for example, by humanization, and so on.

Generally, detection of soluble BAG3 is performed according to a sandwich scheme wherein the soluble protein in the serum interacts with a first molecule immobilized on solid phase (BAG3 ligand, in the capture step) and then with a second molecule which allows direct or indirect colorimetric or fluorimetric detection by binding the soluble BAG3 protein that is already bound to the capture ligand, at the level of a different site. The second ligand is termed detection ligand.

The method also includes a realization of the assay wherein the first capture agent or the second detection agent are adsorbed, adhered or covalently bound to a matrix (also called solid phase), for example a microtiter plate or beads or the wall of a tube.

Alternatively soluble BAG3 can be detected in the serum also after molecular separation (for example by SDS-PAGE) and subsequent antibody recognition, for example by western-blot, or by sequencing of the protein separated on the basis of molecular weight.

The proposed assay method allows separation of the group of cardiac patients from the group of healthy patients, preferably in groups of comparable age. Moreover, it stratifies the same cardiac patients, identifying subpopulations of patients at higher risk (heart failure) with more unfavorable prognosis.

For heart disease a selected pathology of the heart is intended, for example selected from the group consisting of: angina pectoris, unstable angina, myocardial infarction, heart failure, acute coronary disease, acute heart failure, chronic heart failure, heart damage from drugs, etc.

The values of serum BAG3 characteristic of a normal or a pathological state are reported below only as an example because they can vary with the scheme used for the assay. The concentration of soluble BAG3 is on average 2.38 ng/ml±0:32, however in the age group from 21 to 43 years the average serum concentration of BAG3 is 3.13 ng/ml (±0.50), whereas it is 1.80 ng/ml (±0.40) in donors between 44 and 65 years of age.

In sera of patients with clinical diagnosis of heart disease (of various type and grade) the presence of soluble BAG3 protein in an age range comprised between 49 to 81 years (average age: 68.04±6.9), the concentration of BAG3 detected is on average 8.30 ng/ml±0:58.

In patients affected by pancreatic adenocarcinoma, the concentration of soluble BAG-3 is generally higher than 10 ng/ml with an average of 130.8 ng/ml (±59.4). According to a further aspect, the invention concerns the use of the soluble human BAG3 protein as a marker of a pathological condition. In particular, the pathological condition is a heart disease and is selected from the group consisting of: angina pectoris, unstable angina, myocardial infarction, heart failure, acute coronary disease, acute heart failure, chronic heart failure, cardiac iatrogenic damage, etc. or a pancreatic tumor, preferably an adenocarcinoma.

Without being bound to any specific theory, BAG3 secretion by pancreatic cells and cardiomyocytes could represent a "physiological" cellular response to the stress originating, in the case of the heart, from the pathogenic insult and, in the case of pancreatic adenocarcinoma, from deprivation of oxygen and/or other nutrients.

In addition, the invention relates to the use of the soluble human BAG3 protein to activate target cells of the immune system, preferably mammalian macrophages, as BAG3 is a highly conserved protein.

EXPERIMENTAL PART

Example 1

Isolation of AC-1, AC-2, AC-3 Clones from the Parental Hybridoma

Monoclonal antibodies AC-1, 2 and 3 were isolated by sub-cloning from the parental hybridoma, which was deposited with No. PD02009 on Dec. 17, 2002 at the Advanced Biotechnology Center of Genoa and is described in U.S. Pat. No. 7,537,760, and were selected by ELISA assays on the culture medium.

Example 2

Soluble BAG3 Protein is Purified from the Serum of Patients with Heart Disease

The serum of a patient affected by chronic ischemic heart disease was analyzed by western-blotting. The band corresponding to 75 KD was gel-eluted (see FIG. 1a) and the fragments obtained by trypsin digestion were analyzed by mass spectrometry (MALDI/MS) and identified through the "MASCOT" software. The analysis of some peptide sequences (FIG. 1b) allowed identification of the protein as BAG3-like.

Example 3

Development of a Model of Myocardial Stress in Rats

Sprague-Dawley male rats (Charles River Laboratories, Italy), weighing around 220-250 grams, were anesthetized with intraperitoneal injection of pentobarbital (60 mg/kg) orally and then intubated. After anterior thoracotomy, the heart was exteriorized and subjected to suture of the proximal anterior tract of the descending coronary artery. Control animals underwent the same procedure except ligation of the artery. The day after the procedure, all survivors were selected by transthoracic echocardiography for the presence of large infarcts involving at least 35% of the left ventricle (IM group). Rats were then sacrificed by standard procedures and the left ventricle was treated with formalin for immunohistochemical procedures. The figure shows BAG3 protein expression data representative of control and IM groups.

Figure 2:
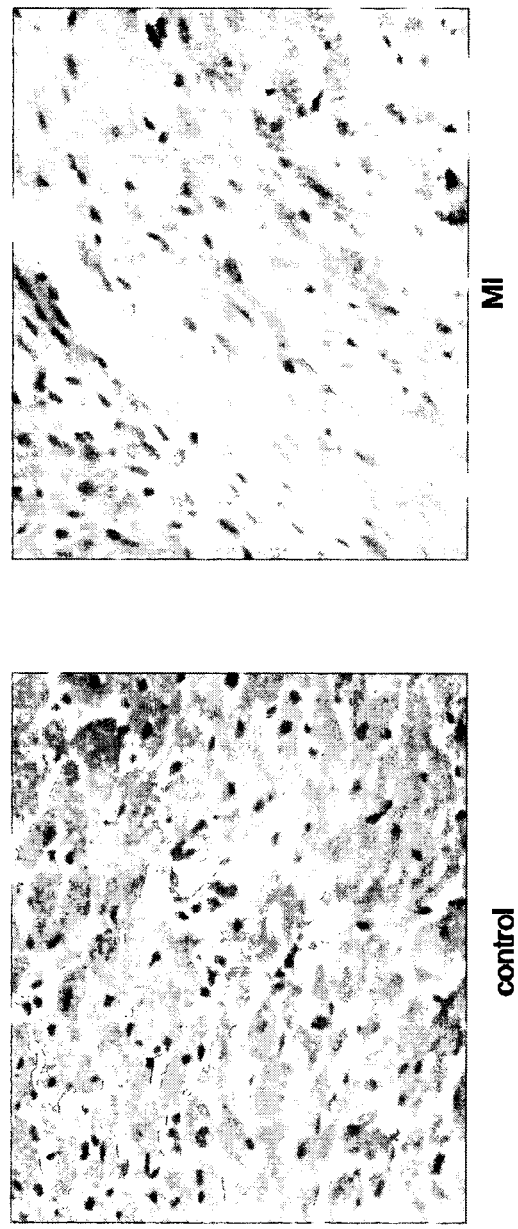
FIG. 2. Western-blot with anti-BAG3 antibodies performed on lysate and supernatants from cardiomyocytes.

FIG. 2 shows the results of immunohistochemistry obtained with a BAG3-specific monoclonal antibody described in Example 1: a significant increase of BAG3 protein levels is observed in heart tissue from rats after induction of infarction by temporary occlusion of the aorta.

Figure 3:
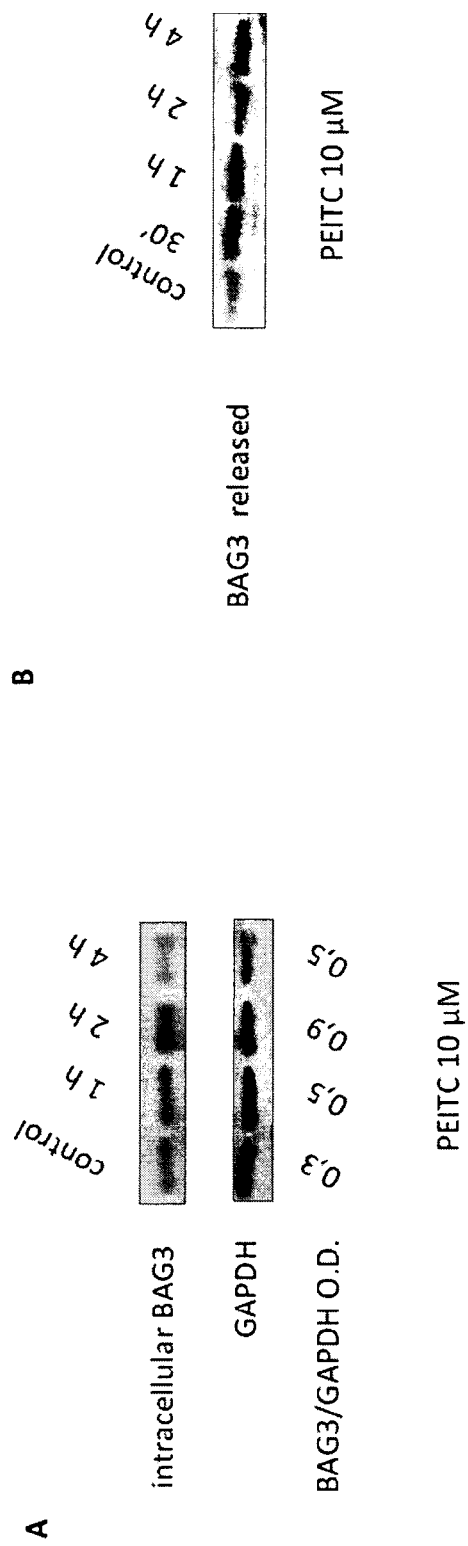
FIG. 3. Western-blot analysis, with anti-BAG3 antibodies, of the soluble protein purified from the serum of a patient with chronic ischemic heart disease.

Western blot analysis then revealed that the BAG3 protein is released in the supernatant of cardiomyocytes exposed to oxidative stress induced by PEITC (phenylisothiocyanate) (FIG. 3).

In this experiment, rat cardiomyocytes, plated at a confluence of 80% and incubated in medium lacking serum at 37° C. in 5% $CO_2$ atmosphere, were treated with 10 µM PEITC for the times indicated in the figure.

At the end of the experiment, cells were harvested and processed. The protein lysate was analyzed by western-blot with anti-BAG3 antibodies (TOS-2 and AC-1) to evaluate the expression levels of intracellular BAG3, and anti-GAPDH antibody used as loading control (FIG. 3A); in FIG. 3B, the supernatants were collected, precipitated with acetone (1:9 vol.) and analyzed by western blotting.

The presence of BAG3 was also detected in the supernatant of Hep G2 (human hepatocellular carcinoma), C6 (rat glioblastoma), Panc-1 (human pancreatic adenocarcinoma), ARO (anaplastic thyroid carcinoma) and HT-29 (colorectal adenocarcinoma) cell lines. BAG3 is released by the various tumor cell lines tested but not in the culture medium of normal primary cells such as HUVEC (human umbilical cord endothelial cells).

Example 4

Development of an ELISA Test for the Measurement of BAG-3 in Serum

To test whether the BAG3 protein was detectable in the blood of patients with heart disease, an ELISA test has been developed using as a calibrator the BAG3 recombinant protein prepared as described below.

The different combinations of BAG3-specific antibodies tested are:

a):
  a first monoclonal antibody clone AC-1 designed to recognize the sequence of aa 18-33 of the BAG3 Protein (DRDPLPPGYEIKIDPQ);
  a second polyclonal antibody termed TOS-2, developed by using as immunogen the whole recombinant protein (RefSeq: NP_004272), was used instead as detector of the BAG3 protein captured by the AC-1 antibody;

b):
  a first monoclonal antibody clone AC-1;
  a second monoclonal antibody termed AC-2, designed to recognize the sequence of aa 385-399 of the BAG3 protein (SSPKSVATEERAAPS) and used as detector;

c):
  a first monoclonal antibody clone AC-1;
  a second monoclonal antibody termed AC-3, designed to recognize the sequence of aa 533-547 of the BAG3 protein (DKGKKNAGNAEDPHT) and used as detector;

d):
  a first monoclonal antibody clone AC-1;
  a mixture of AC-2 and AC-3 antibodies used as detector;

e):
  a first monoclonal antibody clone AC-2;
  as detectors: AC-1, or AC-3, or a mixture of AC-1 and AC-3 antibodies;

f):
  a first monoclonal antibody clone AC-3;
  as detectors: AC-1, or AC-2, or a mixture of AC-1 and AC-2 antibodies.

Figure 4:
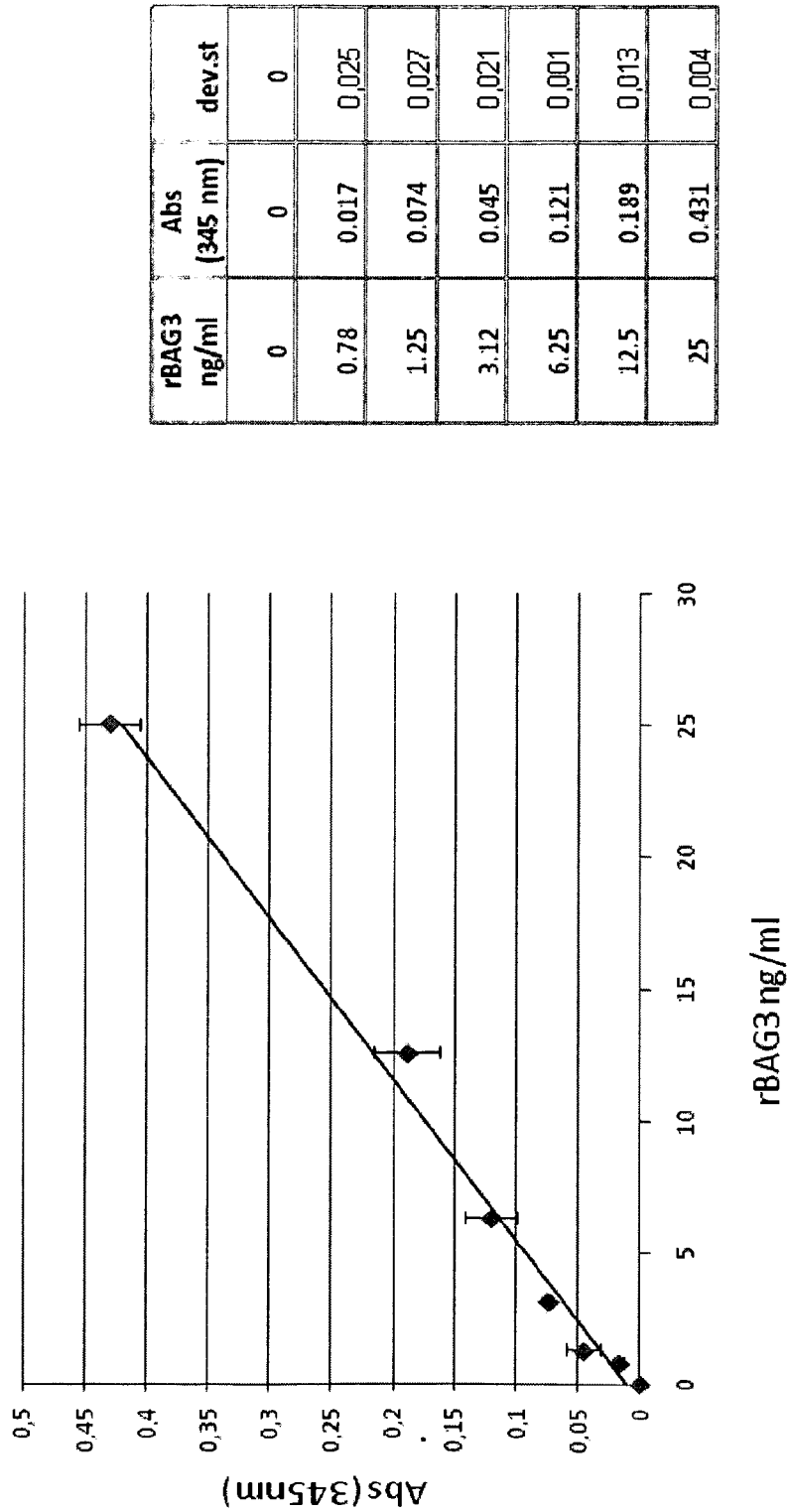
FIG. 4. Calibration curve of ELISA for detection of BAG3.

All combinations tested are able to identify, in a quantitative manner, the presence of soluble BAG-3 in the serum of patients, by the ELISA test. An illustrative example in FIG. 4 shows the development of a calibration curve with scalar concentrations of recombinant BAG3 protein reconstituted in saline solution with the addition of 3% bovine serum albumin (BSA).

The recombinant protein was produced from the cDNA encoding the BAG3 protein, corresponding to nucleotides 1 to 2608 of the NCBI PubMed sequence: NM_004281.3 human, amplified by PCR from total RNA obtained from the breast cancer cell line MCF-7 and then cloned in the expression vector pET 30a (+) (Novagen) using the restriction enzymes NcoI/XhoI.

The resulting recombinant protein fused to six histidine residues was expressed in *E. coli* and purified by affinity chromatography with HisTrap HP columns (GE Healthcare).

96-well microplates were then functionalized by addition of a solution containing the AC-1 antibody and subsequently treated with blocking solution to prevent nonspecific interactions. The recombinant protein was then added at the concentrations shown in the figure, revealed by the polyclonal antibody TOS-2. The signal was obtained by use of an anti-rabbit secondary antibody conjugated to hydroperoxidase (HRP) and subsequent addition of TMB reagent (eBioscience, UK).

The assay proved to be useful to analyze the presence of soluble BAG3 protein in the serum of patients with heart failure.

Example 5

Validation of the ELISA Assay on the Serum of Patients with Heart Disease and Pancreatic Cancer Sera were collected from healthy donors in order to check the serum concentration of BAG3 in subjects not suffering from any kind of overt disease. The age range of donors was from 21 to 65 years. The concentration of BAG3 detected was on average 2.38 ng/ml±0.32.

Figure 5:
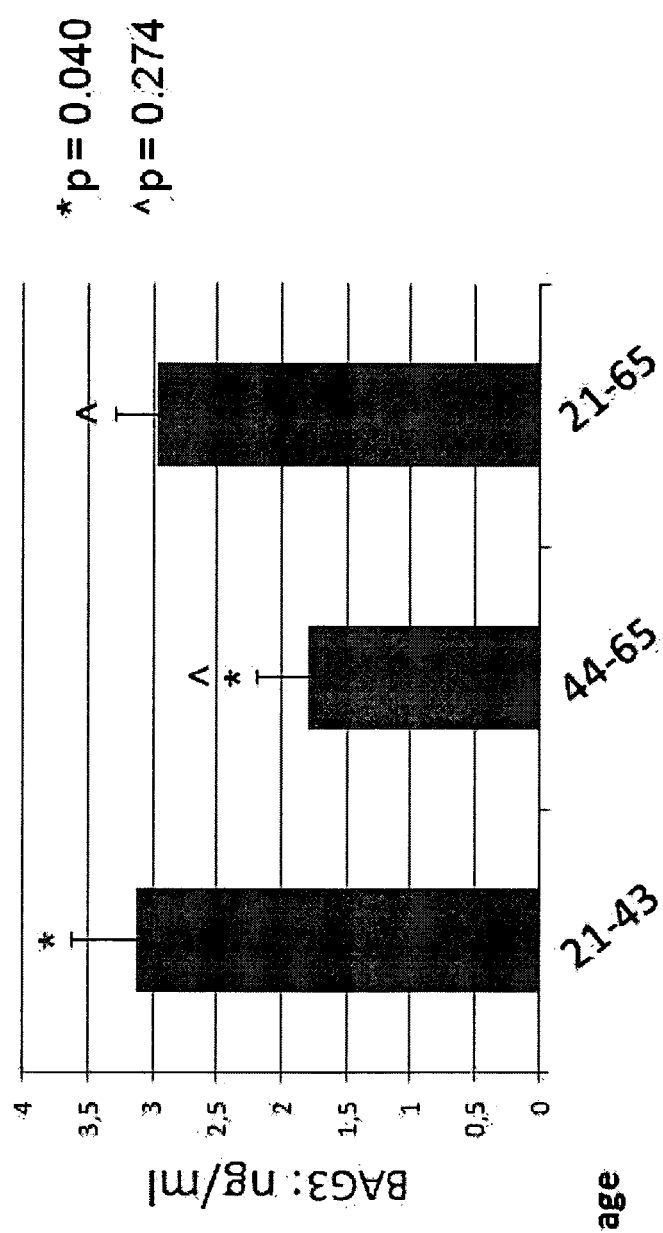
FIG. 5. Graphical representation of BAG3 serum concentrations in healthy donors and according to age groups.

There was a slight, age-related difference of concentrations. In particular, in the 21-43 year age group, the average serum concentration of BAG3 is 3.13 ng/ml (±0.50), whereas it is 1.80 ng/ml (±0.40) in donors between 44 and 65 years of age (FIG. 5).

Then the sera from 38 patients with clinical diagnosis of heart disease (of various type and grade) were collected in order to analyze the presence of soluble BAG3 protein. The age range of the patients examined was comprised between 49 and 81 years (mean age: 68.04±6.9). The concentration of BAG3 detected is on average 8.30 ng/ml±0:58.

Figure 6:
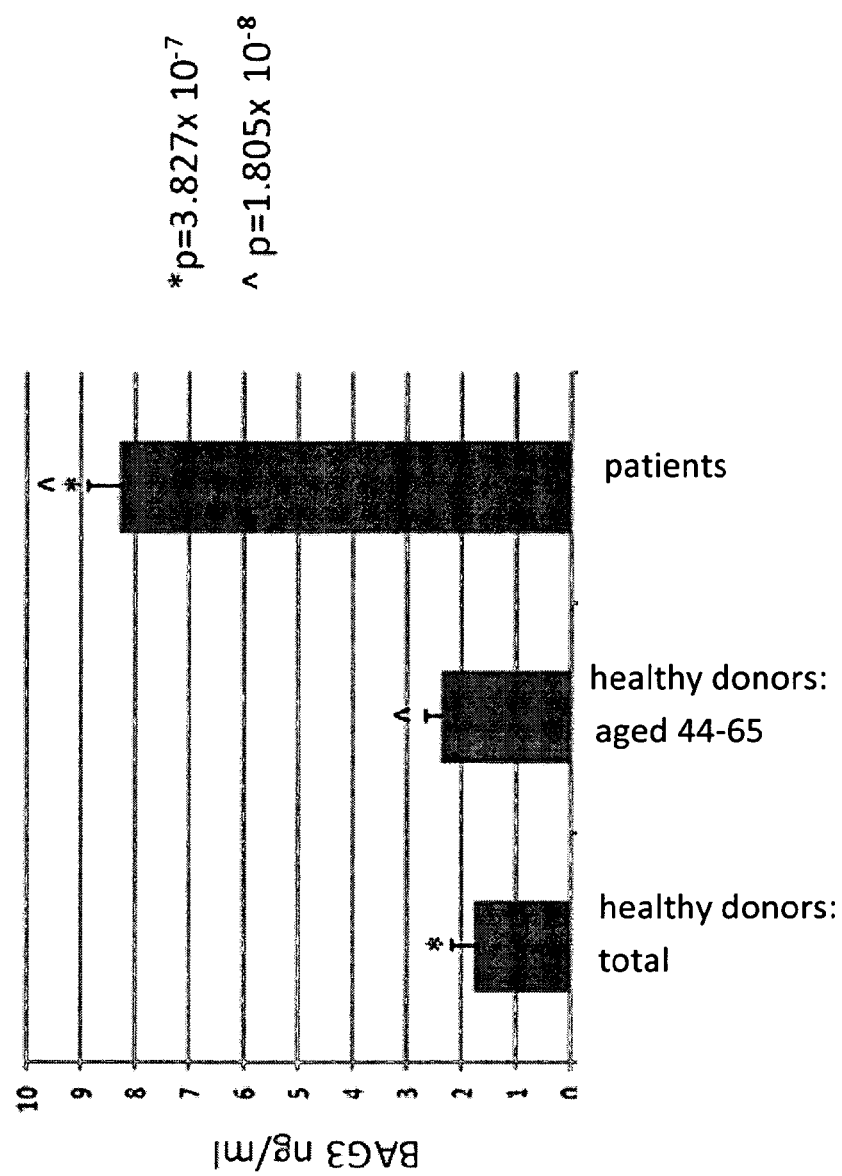
FIG. 6. Graphical representation of BAG3 serum concentrations in healthy donors divided into age groups and in patients.

The difference between patients with heart disease and healthy donors, both total and in the same age range of patients, is highly significant (FIG. 6).

Figure 8:
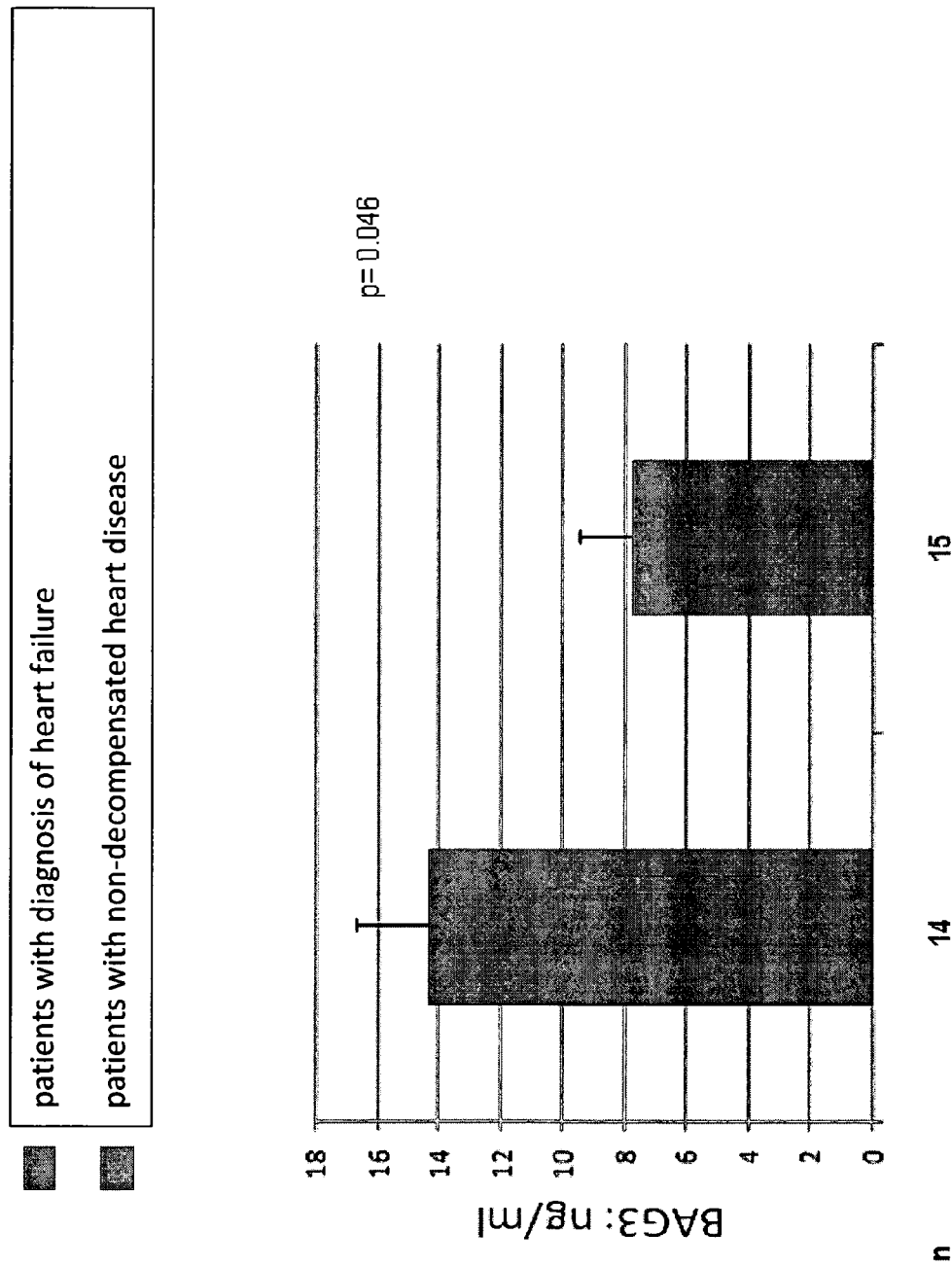
FIG. 8. Graphical representation of BAG3 serum concentrations in patients with diagnosis of heart failure compared to patients with non-decompensated heart disease.

Furthermore, two populations were recognized among patients with heart disease, consisting of subjects with or without heart failure, and characterized by different serum levels of BAG3 protein, as described in FIG. 8 which graphically shows the serum concentrations of BAG3 in patients with diagnosis of heart failure compared to patients with non-decompensated heart disease.

Moreover, the serum levels of soluble BAG-3 were also measured in some patients with pancreatic cancer, colon cancer or lung cancer. Serum levels above 70 ng/ml were only measured in patients with pancreatic cancer, as shown in the following table 1.

TABLE 1

Levels of soluble BAG-3 in sera of cancer patients

| | Serum concentration of BAG-3 (ng/ml) |
|---|---|
| Pancreatic adenocarcinoma | |
| Patient 1 pancreas | 222.5 |
| Patient 2 pancreas | 157.6 |
| Patient 3 pancreas | 102.7 |
| Patient 4 pancreas | 77.4 |
| Patient 5 pancreas | 94 |
| Colon cancer | |
| Patient 1 colon | 0 |
| Patient 2 colon | 0 |
| Patient 3 colon | 0 |
| Lung carcinoma | |
| Patient 1 Lung | 0 |
| Patient 2 Lung | 0 |

Example 6

Determination of Sensitivity and Specificity of the ELISA Assay

The data obtained were then analyzed through a program of statistical analysis in order to define the values of sensitivity and specificity of the ELISA assay for detection of the BAG3 protein in patients with heart failure.

Figure 7:
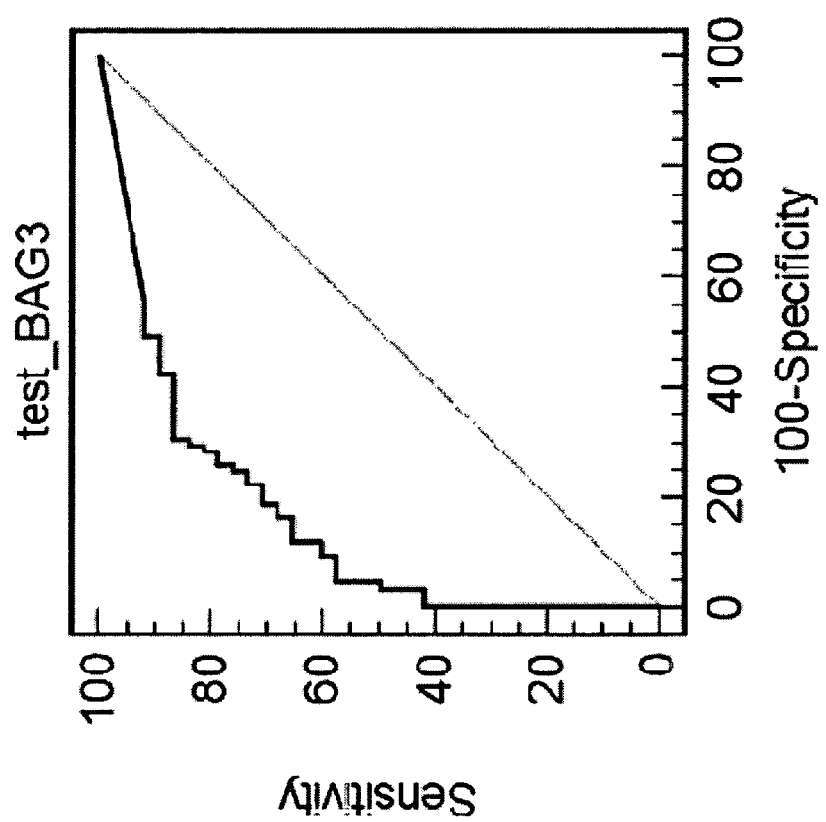
FIG. 7. ROC curve of ELISA test for detection of the BAG3 protein in patients with heart failure.

Using 2.76 ng/ml as cut-off value, sensitivity and specificity values are 83.3% and 77.08%, respectively, while positive and negative predictive values are 75% and 88.1%, respectively. FIG. 7 shows the ROC curve obtained with the indicated cut-off.

Example 7

Characterization of the Functional Activity of the Soluble BAG3 Protein

The recombinant BAG3 protein was used for macrophage activation assays, in order to determine the possible role on blood cells of the protein released in the serum. For this purpose, the murine monocyte J774 cell line was treated with different concentrations of the recombinant BAG3 protein, using a pro-inflammatory agent such as lipopolysaccharide (LPS) as a positive control. J774 cells were plated at 60% confluence and incubated for 24 h with the recombinant BAG3 protein at concentrations of 250, 500 ng/ml and 1 mg/ml, alone or in combination with LPS at a concentration of 10 ng/ml.

At the end of the experiment, cells were harvested and processed. The protein lysate was analyzed by western-blot with anti-iNOS antibodies (iNOS: inducible nitric oxide synthase) to assess the expression levels of the enzyme, and with antibody against GAPDH, used as a loading control. The data are shown in FIG. 9a).

Figure 9:
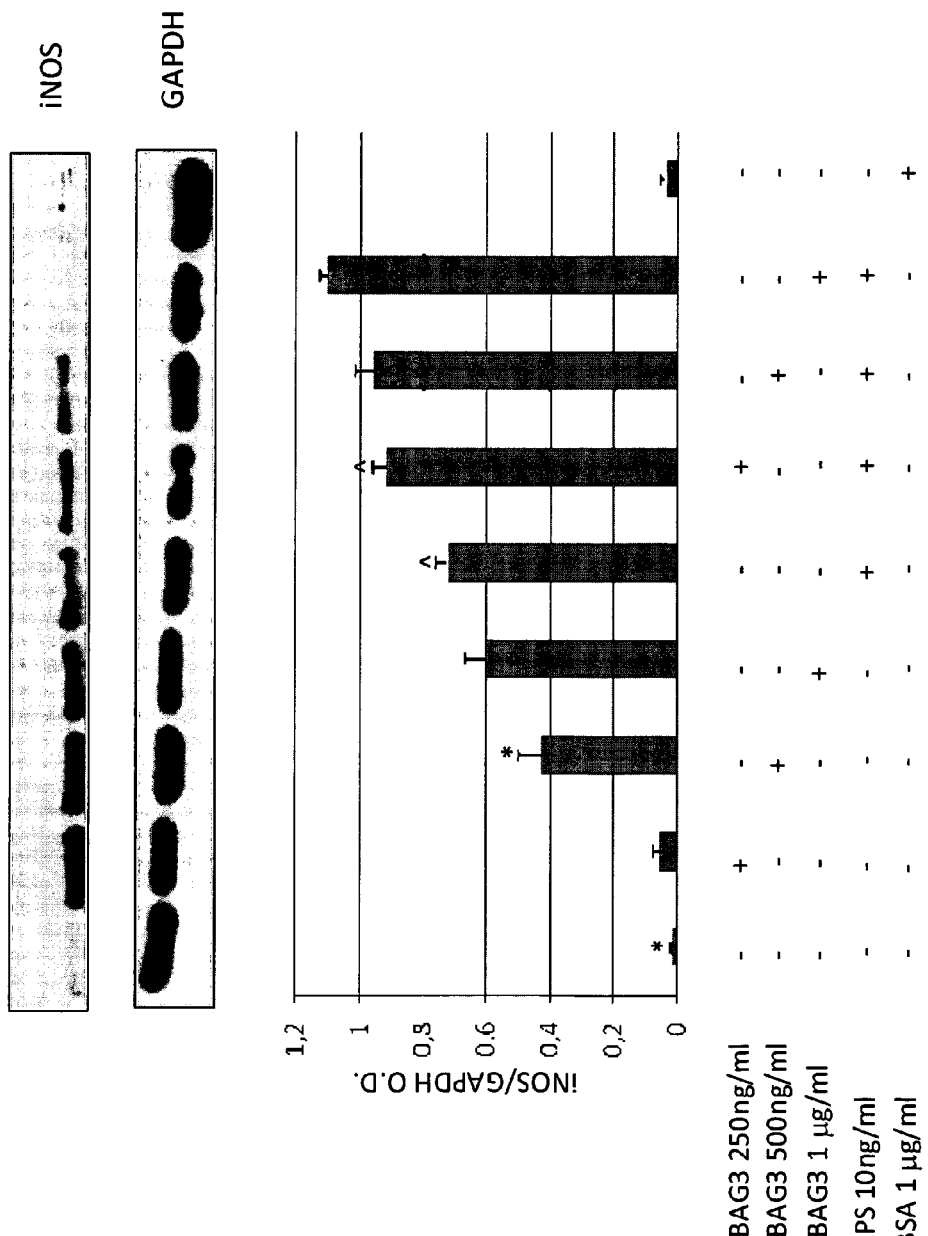
FIG. 9. a) Production of iNOS (inducible nitric oxide synthase) protein and of a control protein for comparison (GAPDH) in murine macrophages (J774) stimulated with increasing doses of soluble recombinant BAG-3 in the presence or absence of LPS, b) determination of nitrite with Griess reagent in the same cell type.
Figure 9:
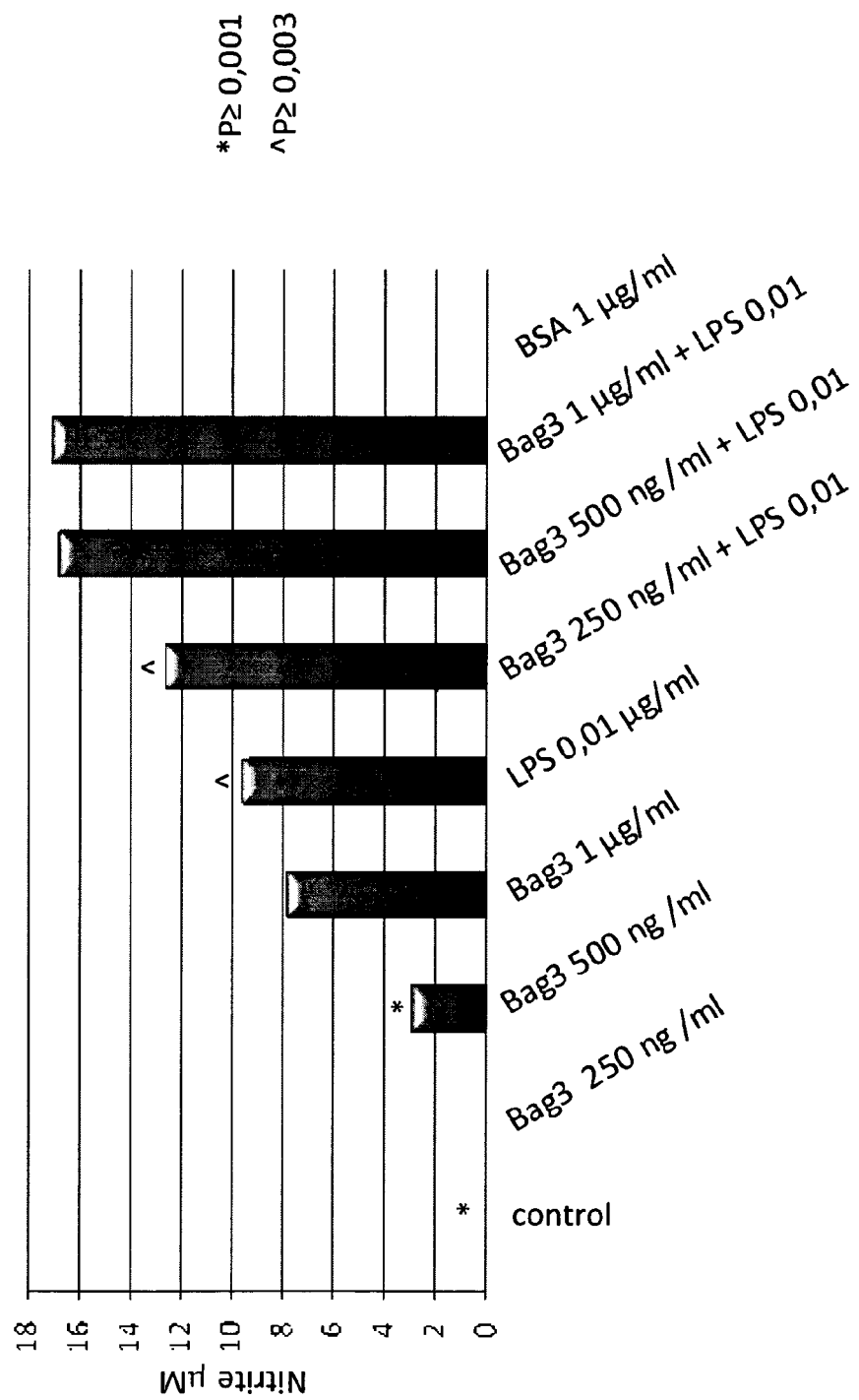

Moreover the production of nitrites in the culture medium, which correlates with monocyte activation, was verified with the Griess reagent (1% sulfanilamide, 0.1% naftilethylenediamine, 5% phosphoric acid) and measured in a Beckman DU-62 spectrophotometer at 550 nM (FIG. 9b).

FIG. 9b) shows that the recombinant protein, at a concentration of 500 ng/ml, increased three-fold the production of nitrites compared to the control (consisting of untreated cells) ($p<0.001$); furthermore its activity is dose-dependent. (FIGS. 9a and b)).

The BAG3 recombinant protein was then conjugated to FITC using the FluoroTag FITC Conjugation Kit (Sigma). Equal amounts of BSA-FITC (negative control) and rBAG3-FITC were added to the culture medium for 1 hour. Cells were then fixed with a solution of 3.7% formaldehyde and analyzed by a Zeiss LSM confocal microscope.

Binding of the BAG3 protein to the surface of J774 cells was confirmed by use of the recombinant protein conjugated with a fluorophore. BAG3 binding is specific because it is not observed when other proteins, for example BSA, are used instead of BAG3.

REFERENCES

1. Bonelli, P., Petrella A., Rosati, A., Romano, M. F., Lerose, R., Pagliuca, M. G., Amelio, T., Festa, M., Martire, G., Venuta, S., Turco, M. C., and Leone, A. (2004). BAG3 protein regulates stress-induced apoptosis in normal and neoplastic leukocytes. Leukemia 18, 358-360.
2. Bruno, A. P., Festa, M., Dal Piaz, F., Rosati, A., Turco, M. C., Giuditta, A., Marzullo, L. (2008). Identification of a synaptosome-associated form of BAG3 protein. Cell Cycle 7(19), 3104-3105.
3. Carra, S., Seguin, S. J., Landry, J. (2008a). HspB8 and Bag3: a new chaperone complex targeting misfolded proteins to macroautophagy. Autophagy 4(2), 237-239.
4. Carra, S., Seguin, S. J., Lambert, H., Landry, J. (2008b). HspB8 chaperone activity toward poly(Q)-containing proteins depends on its association with Bag3, a stimulator of macroautophagy. J Biol Chem 18, 283(3), 1437-1444.
5. Chen, L., Wu, W., Dentchev, T., Zeng, Y., Wang, J., Tsui, I., Tobias, J. W., Bennett, J., Baldwin, D., Dunaief, J. L. (2004). Light damage induced changes in mouse retinal gene expression. Exp Eye Res 79(2), 239-247.
6. Chiappetta, G., Ammirante, M., Basile, A., Rosati, A., Festa, M., Monaco, M., Vuttariello, E., Pasquinelli, R., Arra, C., Zerilli, M., Todaro, M., Stassi, G., Pezzullo, L., Gentilella, A., Tosco, A., Pascale, M., Marzullo, L., Belisario, M. A., Turco, M. C. and Leone, A. (2007). The antiapoptotic protein BAG3 is expressed in thyroid carcinomas and modulates apoptosis mediated by tumor necrosis factor-related apoptosis-inducing ligand. J Clin Endocrinol Metab 92(3), 1159-1163.

7. Franceschelli, S., Rosati, A., Le Rose, R., Turco, M. C., Pascale, M. (2008). Bag3 gene expression is regulated by heat shock factor 1. J Cell Phisiol 19, 215(3), 575-577.
8. Gentilella, A., Passiatore, G., Deshmane, S., Turco, M. C., Khalili, K. (2008). Activation of BAG3 by Egr-1 in response to FGF-2 in neuroblastoma cells. Oncogene 28, 27(37), 5011-5018.
9. Homma, S., Iwasaki, M., Shelton, G. D., Engvall, E., Reed, J. C., Takayama, S. (2006). BAG3 deficiency results in fulminant myopathy and early lethality. Am J Pathol 169 (3), 761-773.
10. Iwasaki, M., Homma, S., Hishiya, A., Dolezal, S. J., Reed, J. C., Takayama, S. (2007). BAG3 regulates motility and adhesion of epithelial cancer cells. Cancer Res1, 67(21), 10252-10259.
11. Kassis, J. N., Guancial, E. A., Doong, H., Virador, V., Kohn, E. C. (2006). CAIR-1/BAG-3 modulates cell adhesion and migration by downregulating activity of focal adhesion proteins. Exp Cell Res 10, 312(15), 2962-2971.
12. Liao, Q., Ozawa, F., Friess, H., Zimmermann, A., Takayama, S., Reed, J. C., Kleeff, J. Buchler, M. W. (2001). The anti-apoptotic protein BAG-3 is overexpressed in pancreatic cancer and induced by heat stress in pancreatic cancer lines. FEBS Lett 503, 151-157.
13. Pagliuca, M. G., Lerose, R., Cigliano, S, and Leone, A. (2003). Regulation by heavy metals and temperature of the human BAG-3 gene, a modulator of Hsp70 activity. FEBS Lett 541, 11-15.
14. Romano, M. F., Festa, M., Putrella, A., Rosati, A., Pascale, M., Bisogni, R., Poggi, L., Kohn, E. C., Venuta, S., Turco, M. C. and Leone, A. (2003b). BAG3 protein regulates cell survival in childhood acute lymphoblastic leukemia cells. Cancer Biol Ther 2, 508-510.
15. Romano, M. F., Festa, M., Pagliuca, G., Lerose, R., Bisogni, R., Chiurazzi, F., Storti, G., Volpe, S., Venuta, S., Turco, M. C. and Leone, A. (2003a). BAG3 protein controls B-chronic lymphocytic leukaemia cell apoptosis. Cell Death Differ 10, 383-385.
16. Rosati, A., Leone, A., Del Valle, L., Amini, S., Khalili, K. and Turco, M. C. (2007a). Evidence for BAG3 modulation of HIV-1 gene transcription. J Cell Physiol 210(3), 676-683.
17. Rosati, A., Ammirante, M., Gentilella, A., Basile, A., Festa, M., Pascale, M., Marzullo, L., Belisario, M. A., Tosco, A., Franceschelli, S., Moltedo, O., Pagliuca, G., Lerose, R. and Turco, M. C. (2007b). Apoptosis inhibition in cancer cells: a novel molecular pathway that involves BAG3 protein. IJBCB 39 7-8, 1337-1342.
18. Tabuchi, S., Asaeda, M., Kamitan, H., Watanabe, T. (2006). Surgical treatment of arteriovenous malformation in a patient with human immunodeficiency virus infection and hemophilia a: case report. J Stroke Cerebrovasc Dis 15(2), 66-8.

The invention claimed is:

1. A method for determining the presence of a pathological condition in a subject comprising the steps of:
   a. measuring the level or concentration values of soluble BAG3 protein in a serum or plasma sample obtained from the subject;
   b. comparing the level or concentration of the soluble BAG3 protein measured in step (a) to a reference level or concentration for the soluble BAG3 protein obtained from a serum or plasma of a healthy subject; and
   (c). associating a significant increase in the level or concentration values of the measured soluble BAG3 over the reference level or concentration for the soluble BAG3 with the presence of the pathological condition in the subject, wherein the pathological condition is chronic ischemic heart disease, heart failure or pancreatic cancer.

2. The method of claim 1 wherein measuring is by immunoassay comprising using specific ligands for soluble BAG3.

3. The method of claim 1 wherein said serum or plasma sample is of human origin.

4. The method of claim 1 wherein anticoagulant substances are added to said serum or plasma sample.

5. The method of claim 2 wherein said specific ligands are antibodies or fragments thereof that bind the soluble BAG3 antigen.

6. The method of claim 5 wherein the antibodies or fragments thereof are monoclonal, polyclonal or recombinant anti-BAG3 antibodies or fragments thereof that bind the soluble BAG3 antigen.

7. The method of claim 6 wherein said antibody is monoclonal and recognizes at least one BAG3 epitope selected from the group consisting of the following amino acid sequences: 18-33 (SEQ ID NO:1), 385-399 (SEQ ID NO:2) or 533-547 (SEQ ID NO:3) of the primary sequence of BAG3 or is a recombinant derivative thereof, humanized or otherwise modified by recombination.

8. The method of claim 2, wherein said ligands are labeled with fluorophores, chromophores or enzymes able to convert a substrate into a chromophore.

9. The method of claim 2 wherein the immunoassay is a sandwich ELISA with a BAG3 capture ligand and a detection ligand, wherein both the capture ligand and the detection ligand are monoclonal antibodies and wherein the detection ligand antibody recognizes an epitope different from the one recognized by the capture ligand antibody used, or is a mixture of several monoclonal antibodies.

10. A method for identifying a subject having heart disease or pancreatic cancer comprising:
   a. measuring the level or concentration values of soluble BAG3 protein in a serum or plasma sample obtained from the subject, wherein the level or concentration values of soluble BAG3 are measured by immunoassay;
   b. comparing the level or concentration of the soluble BAG3 protein measured in step a to a reference level or concentration for the soluble BAG3 protein obtained from serum or plasma of a healthy subject;
   c. identifying the subject as having heart disease or pancreatic cancer if the level or concentration values of the measured soluble BAG3 are significantly higher than the level or concentration values of the reference level or concentration values for the soluble BAG3.

11. The method of claim 5, wherein the antibody fragments comprise scFv, diabodies, or minibodies.

* * * * *

```
SEQUENCE LISTING

<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Asp Arg Asp Pro Leu Pro Pro Gly Trp Glu Ile Lys Ile Asp Pro Gln
1               5                   10                  15

<210> SEQ ID NO 2
<211> LENGTH: 15
<212> TYPE: PRT
<213> ORGANISM: Homo sapiens

<400> SEQUENCE: 2

Ser Ser Pro Lys Ser Val Ala Thr Glu Glu Arg Ala Ala Pro Ser
1               5                   10                  15

<210> SEQ ID NO 3
<211> LENGTH: 15
<212> TYPE: PRT
<213> ORGANISM: Homo sapiens

<400> SEQUENCE: 3

Asp Lys Gly Lys Lys Asn Ala Gly Asn Ala Glu Asp Pro His Thr
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: synthetic construct; fragment of BAG3-like
      protein
```

-continued

```
<400> SEQUENCE: 4

Lys Ile Asp Pro Gln Thr Gly Trp Pro Phe Phe Val Asp His Asn Ser
1               5                   10                  15

Arg Thr

<210> SEQ ID NO 5
<211> LENGTH: 10
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 5

Arg Thr Thr Thr Trp Asn Asp Pro Arg Val
1               5                   10

<210> SEQ ID NO 6
<211> LENGTH: 13
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 6

Lys Asp Thr Ala Ser Ser Ala Asn Gly Pro Ser Arg Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 7

Arg Leu Leu Pro Ile Arg Glu
1               5

<210> SEQ ID NO 8
<211> LENGTH: 17
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 8

Arg Gln Pro His Leu Phe His Ala Tyr Ser Gln Pro Gly Val Gln Arg
1               5                   10                  15

Phe

<210> SEQ ID NO 9
<211> LENGTH: 12
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 9

Arg Ser Ser Leu Gly Ser His Gln Leu Pro Arg Gly
1               5                   10
```

```
<210> SEQ ID NO 10
<211> LENGTH: 14
<212> TYPE: PRT
<213> ORGANISM: Artificial Sequence
<220> FEATURE:
<223> OTHER INFORMATION: synthetic construct; fragment of BAG3-like
      protein

<400> SEQUENCE: 10

Lys Ile Gln Gly Asp Asp Trp Glu Pro Arg Pro Leu Arg Ala
1               5                   10
```